(12) United States Patent  
Sagberg et al.

(10) Patent No.: US 11,892,396 B2
(45) Date of Patent: Feb. 6, 2024

(54) GAS SENSOR WITH TWO SWITCHABLE FILTERS AND METHOD FOR OPERATING SUCH A GAS SENSOR

(71) Applicant: Dräger Safety AG & Co. KGaA, Lübeck (DE)

(72) Inventors: Håkon Sagberg, Oslo (NO); Britta Greenberg-Fismen, Oslo (NO); Thor Christian Hobæk, Oslo (NO)

(73) Assignee: Dräger Safety AG & Co. KGaA, Lübeck (DE)

( * ) Notice: Subject to any disclaimer, the term of this patent is extended or adjusted under 35 U.S.C. 154(b) by 424 days.

(21) Appl. No.: 17/312,843

(22) PCT Filed: Dec. 12, 2019

(86) PCT No.: PCT/EP2019/084863
§ 371 (c)(1),
(2) Date: Jun. 10, 2021

(87) PCT Pub. No.: WO2020/120663
PCT Pub. Date: Jun. 18, 2020

(65) Prior Publication Data
US 2022/0042903 A1    Feb. 10, 2022

(30) Foreign Application Priority Data

Dec. 13, 2018  (GB) ..................................... 1820293

(51) Int. Cl.
*G01N 21/15* (2006.01)
*G01N 21/31* (2006.01)
*G01N 33/00* (2006.01)

(52) U.S. Cl.
CPC ............. *G01N 21/15* (2013.01); *G01N 21/31* (2013.01); *G01N 33/0029* (2013.01); *G01N 2021/158* (2013.01)

(58) Field of Classification Search
CPC ....... B60Q 1/0088; B60Q 1/52; B60W 40/02; B60W 40/105; B60Y 2400/301;
(Continued)

(56) References Cited

U.S. PATENT DOCUMENTS 5,055,690 A   10/1991  Bonne
7,286,292 B2   8/2007  Sagberg et al.
(Continued)

FOREIGN PATENT DOCUMENTS

EP   0243139 A2   10/1987
EP   2444791 A1   4/2012
(Continued)

*Primary Examiner* — Tri T Ton
(74) *Attorney, Agent, or Firm* — McGlew and Tuttle, P.C.

(57) ABSTRACT

A gas sensor (2) distinguishes between a target gas and a contaminant and includes a light source (8), a measurement volume (4), a detector (22), and an adaptable filter system (20) with a first optical filter and a second optical filter. The filter system switches between a first composite state, with both filters in a reference state, a second composite state, with the first filter in a first reference state and the second filter in a second measurement state, a third composite state with the first filter in a first measurement state and the second filter in a second reference state, and a fourth composite state, with both filters in a measurement state. The gas sensor detects a target gas and makes a determination as to a presence of the contaminant by comparing the respective detector signals, generated during at least three of the composite states, with each other.

15 Claims, 8 Drawing Sheets

(58) Field of Classification Search
CPC ....... B60Y 2400/303; G01N 2021/157; G01N 2021/158; G01N 2021/3148; G01N 2021/3177; G01N 21/031; G01N 21/15; G01N 21/31; G01N 21/314; G01N 21/3504; G01N 33/0029
USPC ..... 356/300–334, 3.04, 3.06, 4.06, 5.02, 28, 356/34, 400, 37, 411, 445, 435, 442, 444, 356/222, 225, 226
See application file for complete search history.

(56) References Cited

U.S. PATENT DOCUMENTS

| | | | |
|---|---|---|---|
| 7,463,420 | B2 | 12/2008 | Sagberg et al. |
| 8,373,568 | B2 | 12/2013 | Moe et al. |
| 2006/0139647 | A1 | 6/2006 | Tice |
| 2012/0243095 | A1 | 9/2012 | Sagberg et al. |
| 2014/0198315 | A1 | 7/2014 | Priore et al. |
| 2018/0074211 | A1* | 3/2018 | Niesen ................. G01S 19/426 |
| 2018/0202920 | A1 | 7/2018 | Borgen et al. |

FOREIGN PATENT DOCUMENTS

| | | | |
|---|---|---|---|
| GB | 2497295 | A | 6/2013 |
| GB | 2497296 | A | 6/2013 |

\* cited by examiner

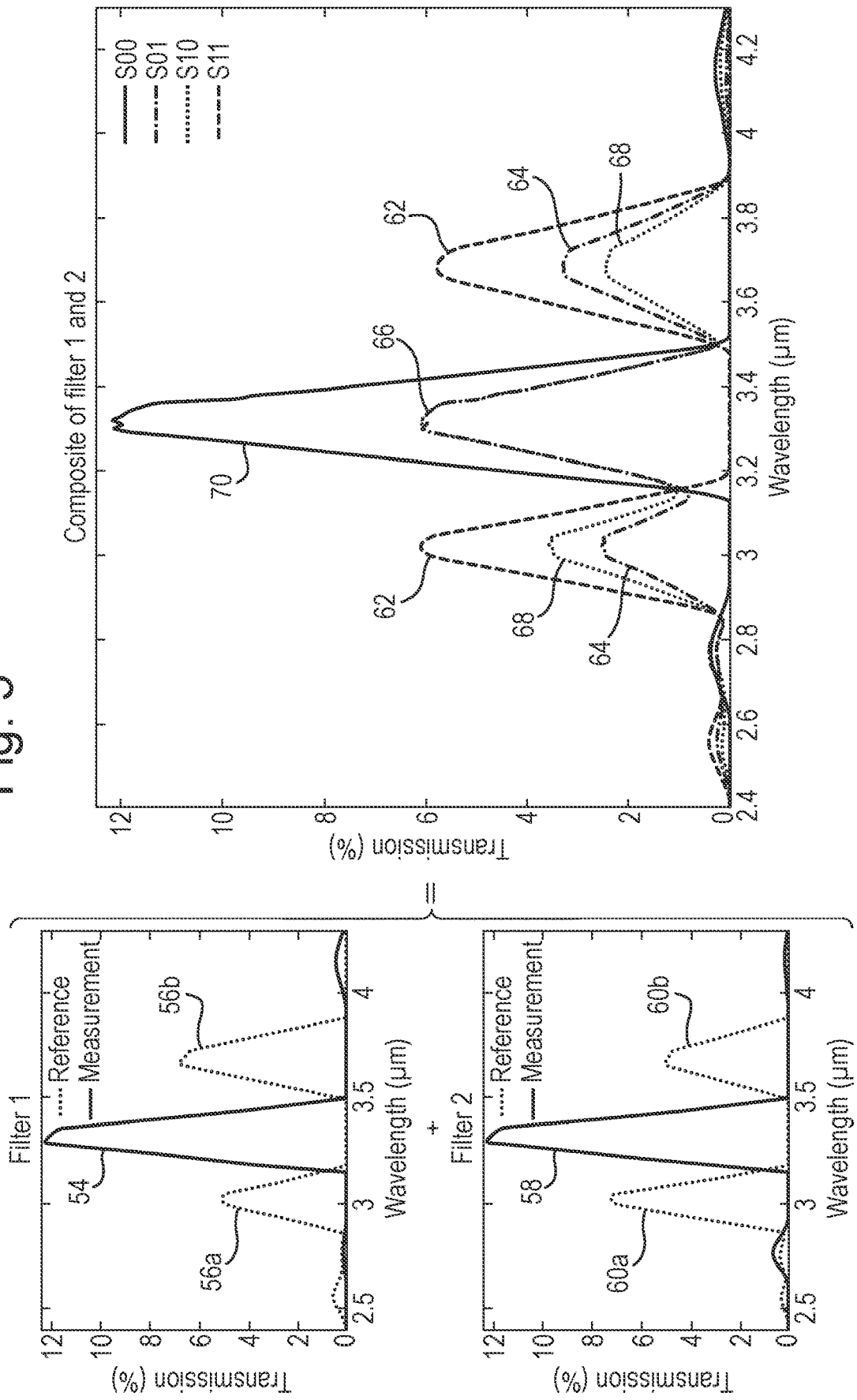

GAS SENSOR WITH TWO SWITCHABLE FILTERS AND METHOD FOR OPERATING SUCH A GAS SENSOR

CROSS REFERENCE TO RELATED APPLICATIONS

This application is a United States National Phase Application of International Application PCT/EP2019/084863, filed Dec. 12, 2019, and claims the benefit of priority under 35 U.S.C. § 119 of UNITED KINGDOM Application 1820293.7, filed Dec. 13, 2018, the entire contents of which are incorporated herein by reference.

TECHNICAL FIELD

The invention refers to a gas sensor and a method for operating such a gas sensor wherein the gas sensor can detect a target gas and can distinguish the target gas from a contaminant, e.g. water.

TECHNICAL BACKGROUND

Gas sensors are used in a variety of environments where it is necessary or desired to detect the presence of at least one target gas. An important example are production plants where explosive gases are handled. It is essential to monitor the surrounding area to detect immediately if explosive gas leaks from a part of the plant and may cause an explosion due to ignition.

A type of gas sensor known in the art determines the presence of a gas by detecting changes in the spectrum of electromagnetic radiation due to absorption by the gas. Such a gas sensor typically comprises a gas measurement volume contained within a gas sensor housing. The housing has apertures to allow gas to pass in and out of the gas measurement volume. Electromagnetic radiation is passed through the gas measurement volume from a radiation source to a radiation detector. The electromagnetic radiation has a frequency band spectrum that covers frequencies corresponding to an absorption band of the target gas of interest. The frequency spectrum received at the detector is analyzed to determine whether any radiation has been absorbed within the absorption band frequency range. If radiation has been absorbed in the absorption band frequency range, this indicates that the gas of interest may be present in the gas measurement volume. The analysis of the frequency spectrum of the electromagnetic radiation may involve comparing the absorption at frequencies in an absorption band with the absorption at frequencies within a reference band, where the reference band is a portion of the frequency spectrum of the electromagnetic radiation that is not absorbed by the gas of interest. In one embodiment a gas sensor according to the invention also uses this principle.

GB 2497296 A shows a gas sensor which measures the concentration of a predetermined gas. An adaptable filter 6 is disposed between the light source and the detector and can be switched between a measurement state and a reference state. In the measurement state a wavelength which is absorbed by the gas passes the filter. In the reference state this wavelength is attenuated. The filter can have more than two states.

Gas sensors are also described in US 2014/0198315 A1 and EP 2444791 A1.

SUMMARY

An object of the invention is to provide a gas sensor and a method for operating a gas sensor which detect a target gas with a lower rate of false events than known gas sensors and operating methods.

This object is solved by a gas sensor according to the invention. The gas sensor according to the invention is configured to detect at least one target gas. It will therefore be appreciated that the gas sensor may be a multi-gas sensor, i.e. it may give a positive alarm if any one or more of a plurality of target gases is/are present.

The gas sensor according to the invention comprises a light source configured to emit light, a measurement volume, a detector configured to receive light and to generate signals depending on the received light, and an adaptable filter system.

The measurement volume and the adaptable filter system are disposed in a light path between the light source and the detector. A light beam passing the light path may be reflected at least one time.

The adaptable filter system comprises a first optical filter and a second optical filter. The first optical filter can be switched between a first reference state in which the first filter passes light according to a first reference wavelength profile and a first measurement state in which the first filter passes light according to a first measurement wavelength profile.

The second optical filter can be switched between a second reference state in which the second filter passes light according to a second reference wavelength profile and a second measurement state in which the second filter passes light according to a second measurement wavelength profile.

The first reference wavelength profile is different from the second reference wavelength profile.

The two optical filters can be switched between these two states per filter independently from each other. The adaptable filter system can therefore be switched between at least four composite states. The potential composite states comprise the following: a first composite state in which the first and second filters are in the first and second reference states respectively; a second composite state in which the first filter is in the first reference state and the second filter is in the second measurement state; a third composite state in which the first filter is in the first measurement state and the second filter is in the second reference state; and a fourth composite state in which the first and second filters are in the first and second measurement states respectively.

The gas sensor can be operated as follows and the method comprises the following steps: the light source emits light; the emitted light passes along the light path through the measurement volume to the detector; the gas sensor switches the adaptable filter system between at least three of the composite states; the detector generates one respective signal corresponding to light received by the detector and referring to one composite state, i.e. in sum at least three signals; the gas sensor determines about the presence of a contaminant other than the target gas in the light path between the light source and the detector. For this determination the gas sensor uses at least three detector signals, namely at least one detector signal for every achieved composite state.

The invention further refers to an adaptable filter system comprising two optical filter elements wherein the adaptable filter system can be switched between at least four composite states.

Advantages of the gas sensor are also advantages of the adaptive filter system and of the operating method and vice versa.

The gas sensor according to the invention can be used in applications where the ambient atmosphere can enter the measurement volume of the gas sensor. Thereby it is possible to detect a target gas in the ambient atmosphere. It cannot be excluded, however, that a contaminant enters the measuring volume or otherwise affects the sensing results.

The term "light source" may denote every source which can emit suitable electromagnetic waves or radiations, in particular light in the visible light spectrum or infrared or ultraviolet light.

The term "measurement volume" as used herein may refer to a region or volume of space in or through which a test gas composition (i.e. a gas that is to be tested for the presence of one or more target gases) flows during use of the gas sensor. It is therefore to be understood that the measurement volume may be an enclosed space, e.g. enclosed by a housing having apertures for the ingress of gas and optionally at least one window or aperture for light, or it may be an open space, e.g. a region passed by a light path from the light source to the detector in an open-path gas sensor.

The terms "measurement wavelength" and "reference wavelength" are defined with respect to the absorption band of the or one target gas. The measurement wavelength profile contains electromagnetic wavelengths (frequencies) that overlap with the absorption spectrum of the target gas. The reference wavelength profile contains electromagnetic wavelengths (frequencies) that are not absorbed by the or one target gas. Ideally the gas sensor operates as follows: When both filters are in the respective reference states and the spectrum received by the detector is one reference wavelength profile, there is no detectable change when the target gas is present in the measurement volume compared to when it is not.

The gas sensor is configured to detect at least one target gas in the measurement volume and to distinguish the or at least one target gas from a contaminant. In general, the gas sensor triggers an alarm if a target gas is detected. The term "contaminant" refers to any gas or further substance which is different from the target gas, may occur in the light path, and should not be perceived as a target gas. Distinguishing between target gas and contaminant reduces the number of false alarms. A large number of false alarms bears the risk that true alarms are ignored.

According to the invention the second reference wavelength differs from the first reference wavelength. Therefore, two different reference states of the filter system are provided. The invention therefore provides the following advantage over a filter system with only one reference state: It may be that the contaminant absorbs or attenuates light in the single reference wavelength. This could even lead to a larger attenuation of the detector signal in the measurement state compared with the reference state. This may in particular happen in the case of water condensate. A filter system with only one reference state can often not at all or not reliably enough distinguish such a contaminant from a target gas. A gas sensor with such a filter system may cause false positive alarms. The filter system according to the invention provides more information about which part of the reference wavelength profile is attenuated. Therefore, the gas sensor according to the invention can better distinguish between the or at least one target gas and a contaminant—even if the optical properties of the contaminant are not exactly known in advance or different contaminants may occur.

If a contaminant that enters the measurement volume of a conventional gas sensor has an absorption profile which overlaps with the absorption band of the target gas, this may result in a false positive alarm, i.e. it appears that a target gas is present when in fact it is not. Similarly, a contaminant having an absorption profile that overlaps with the reference band may result in a false negative or false positive alarm. Comparing the detected radiation in the target gas absorption band with a reference measurement, as described above, does not compensate for this because the absorption and reference measurements are affected differently. The gas sensor according to the invention can automatically detect such a contaminant and thereby avoid some disadvantages of the prior art.

Water or a composition of water and other substances are examples of a contaminant that may enter or otherwise affect the measurement volume. In a conventional gas sensor as well as in a gas sensor according to the invention it is common for the electromagnetic radiation to be passed through or reflected from optical elements such as windows and mirrors and diffusors. In certain environmental conditions, where water has entered the measurement volume, condensation can form on the optical elements. The condensation may absorb or scatter the gas sensor radiation, affecting the spectrum of radiation that is transmitted or reflected to the detector. The amount of absorption or scattering due to condensation on the optical elements is typically not predictable and therefore cannot be accounted for when trying to determine whether or not a target gas is present. In such circumstances, it can be difficult or impossible for a conventional gas sensor to reliably determine whether or not a target gas is present. Condensation or other contaminants may therefore cause false positive alarms or may result in the gas sensor failing to detect the presence of a gas. The former case is at least inconvenient, as it may lead a person monitoring the system to believe that there is a dangerous gas condition present when there is not, and the latter situation can be potentially dangerous if a dangerous gas leak goes undetected because the gas sensor has condensation on its optical elements or another contaminant in the measurement volume.

A potential solution to overcome this problem is to provide a heating element in thermal contact with an object in the light path, preferably a heating system being in thermal contact with each optical element. The optical element may be a window, a lens, a diffusor, or a mirror, e.g. When the temperature of the surface of an optical element is lower than the dew point of water, water vapor will condense on the surfaces of the optical elements. As well known, the dew point depends on the temperature of the ambient air and the humidity level. When this occurs, the condensation can be prevented, reduced or removed by switching on the heating elements in contact with the optical elements. The heating elements transfer thermal energy to the optical elements, thereby raising their temperature. Once their temperature is higher than the ambient temperature, condensation on the optical elements evaporates. The invention can be combined with such a heating element and can be used for reducing the heating time as explained below.

According to the invention the first reference wavelength profile is different from the second reference wavelength profile. The difference may comprise different shapes of the profile or sidebands with different shapes or different positions or distances with respect to a maximum. Preferably the superposition of both reference wavelength profiles has a symmetric shape. Thereby the filter system operated in the first composite state (both filters are in the respective reference states) has a symmetric wavelength profile.

The first measurement wavelength profile may be the same as or different from the second measurement wavelength profile. Using two different measurement wavelength profiles may lead to a gas sensor which can even better distinguish between the target gas and a contaminant. Ideally no target gas absorbs light in one reference wavelength profile.

In some applications the first measurement wavelength profile is adapted to a first target gas, i.e. overlaps with the absorption spectrum of the first target gas. The second measurement wavelength profile is adapted to a second target gas, i.e. overlaps with the absorption spectrum of the second target gas. The same gas sensor according to this embodiment may be used for detecting the first target gas or the second target gas or both and may distinguish them from each other and from a contaminant.

In one embodiment at least one reference wavelength is adapted to a contaminant which may condense on a surface of an object, e.g. a window in the path from the light source to the detector. This contaminant may be or comprise water, e.g. in the form of raindrops or fog, and may further comprise particles solved in the water, e.g. salt. The contaminant may also comprise dust or smoke or fume or oil. Thanks to the invention different embodiments how to reduce in many cases the influence of such a contaminant on the measurement results are possible.

According to one embodiment of the invention the detection of such a contaminant and/or the detection of a suspicious event, e.g. of an attenuation of the emitted light beam, automatically triggers the step that a cleaning device is switched on and removes at least partially a contaminant from an object which is in the path between the light source and the detector, in particular on an optical element in a sensor housing. In one implementation the cleaning device comprises: a cleaning element, e.g. a wiper, brush, blower, or fan, which can remove moisture and/or dust from a surface, in particular from a window, in a contacting or contactless manner; and a controllable drive for the cleaning element.

The cleaning element can also comprise a source for surface acoustic waves which can clean a surface in a contactless manner.

In one implementation the cleaning device comprises a heating element which is in thermal contact with the or at least one object in the light path. The detection of the suspicious event (attenuation) or positively of a contaminant triggers the step that the heating element is switched on and evaporates the contaminant from the surface of the object. If the gas sensor generates an alarm after the contaminant is evaporated, indeed a target gas is detected. In a further implementation the cleaning device comprises a wiping or brushing element or a blowing unit which mechanically removes contaminant from the object's surface.

This embodiment has one further advantage over known sensors in particular when several gas sensors according to the embodiment are distributed in remote locations, for example in networks of distributed wireless remote sensor units. In such cases, it may not be possible or practicable to provide a mains connection, and so the remote sensor units are typically battery powered. In many applications, the purpose of remote sensor networks is to provide ongoing (i.e. medium or long term) monitoring to detect the presence of at least one target gas for safety applications. Accordingly, it is important to ensure that there is an ongoing power supply to the sensors, as a dangerous gas detection failure may occur if the power runs out, and it is inconvenient or even impossible to have to replace the batteries frequently. As such, it is desirable to avoid unnecessary depletion of the battery. Superfluous or continuous use of heating elements is therefore undesirable as it leads to rapid depletion of the battery power. In implementations that use a permanently activated heater to remove condensation, such rapid depletion is more likely to occur because the heater would typically be applied every time there is a non-zero gas concentration measurement (suspicious event) in order to check that it is not a false positive alarm caused by condensation. Some conventional gas sensors may require such a permanently activated heating element in applications where a low concentration of gas normally occurs, and a higher concentration must be detected. The embodiment ensures or at least makes it possible that the heating element is only switched on if a suspicious event (attenuation) or positively a contaminant is detected, and evaporation of contaminant is necessary.

The invention avoids the need of permanently heating an object in the light path for avoiding water or a further contaminant to condense on an object in the light path. Therefore, the energy consumption and the wear of the heating element is reduced—compared with a potential mode in which the heating element is permanently active. The lifetime of a local energy source for a remote gas sensor is prolongated compared with conventional gas sensors.

A potential mode of reducing the influence of a contaminant may be the following operation: If a positive alarm (significant attenuation in the measurement wavelength profile) is detected, the or every heating element is switched on and the measurement is repeated for approving or rejecting the first measurement. This mode of operation may cause a delay. Such a delay may be harmful if target gas really occurs. The energy consumption is increased which is in particular a disadvantage if the sensor is battery-powered. The invention may be combined with such an operation, e.g. for further confirming an alarm, but in many cases avoids the need of such a confirmation. The invention reduces the number of false positive alarms. If a positive alarm triggers the step of switching on the heating element, the invention reduces the energy consumption caused by the heating element as often the heating element needs to be activated for a shorter time period. In many cases the invention enables to securely distinguish between the target gas and the contaminant such that the heating element only needs to be activated less times.

According to one embodiment of the invention a heating element is triggered if a contaminant is detected. According to a further embodiment an alarm is generated showing that the results of the gas sensor are less reliable. This alarm may cause a human to clean the optical elements etc. This further embodiment is in particular useful if not enough electrical energy for operating the heating element is available. In one embodiment the heating element is only activated if a contaminant is detected with sufficient reliability.

In a further embodiment the gas sensor comprises a cleaning device, e.g. a wiper or brush or blower or source for acoustic waves. Thanks to the invention this cleaning device needs only to be activated if a contaminant is actually detected.

Seen in the direction of the light path from the light source to the detector the measurement volume can be positioned before or after the filter system.

In many cases the gas sensor according to the embodiment can automatically and directly derive from the detector signals whether a suspicious event (attenuation) is in fact a target gas or only a (harmless) contaminant. This leads to faster reporting of genuine target gas conditions and to reduce false alarms.

Preferably at least one reference wavelength profile is adapted to a contaminant. In a set of embodiments, the wavelength profile of at least one of the first and second reference wavelength profiles is asymmetric. Both of the first and second reference wavelength profiles may be asymmetric, also in different manners. These possibilities are advantageous because an asymmetric wavelength profile means that the composite states including that wavelength profile will also be asymmetric. Radiation passed during that composite state will therefore have a different optical power at short wavelengths compared with long wavelengths. For example, if a composite state comprises a reference wavelength profile that has a greater transmissivity at short wavelengths than long wavelengths, when the filter system is in that composite state, it will pass more radiation at short wavelengths than at long wavelengths. If this is used in conjunction with a composite state that passes, for example, more radiation at long wavelengths than at short wavelengths, respective portions of radiation passed by the filter system in these composite states will have different amounts of short and long wavelength radiation. Those portions will therefore be affected differently by contaminants such as water whose absorption spectrum is asymmetric with respect to the gas measurement band. For example, water absorbs more strongly at short wavelengths, so the portion of light having greater optical power at short wavelengths will be attenuated proportionately more than the portion of radiation having greater optical power at long wavelengths. This difference in attenuation between the composite states allows the presence of a contaminant like water to be determined and compensated for.

Although preferred, it is not essential for the wavelength profiles to be asymmetric. For example, the respective reference wavelength profiles could comprise sidebands, where, in one of the reference wavelength profiles, the sidebands are spaced further apart than in the other. In that case, the difference in absorption for the composite states would result from a sideband being generally at a shorter wavelength than a corresponding sideband in the other reference profile. It is also possible that the reference wavelength profiles are shifted towards shorter wavelength without necessarily increasing the spacing in between the two bands.

Preferably each reference wavelength profile comprises at least two sidebands. The first and second reference wavelength profiles may each comprise two sidebands. For example, the first reference wavelength profile may comprise two sidebands positioned either side of the frequency of a peak in the first measurement wavelength profile. Similarly, the second reference wavelength profile may comprise two sidebands positioned either side of the frequency of a peak in the second measurement wavelength profile. Where one or both of the first and second reference wavelength profiles is asymmetric, said reference wavelength profile(s) may comprise one larger sideband and one smaller sideband.

A gas sensor according to the embodiment with two sidebands per reference wavelength profile is more robust against shifts in temperature or humidity in the light source or shifts of other properties of the gas sensor or other environmental influences.

One possible implantation is to use extreme asymmetry: In the first reference wavelength profile most or even all optical power is shifted to the short wavelength band whereas in the second reference wavelength profile most or even all optical power is shifted to the long wavelength band. Each reference profile consists of practically only one sideband.

The at least three composite states used by the gas sensor may be the first, second and third or fourth composite states. This combination is particularly convenient, e.g. for analysis, but other combinations are possible, e.g. the second, third and further composite states may be used. More than three composite states may be used, e.g. all four composite states could be used.

It is possible that one filter can be switched into at least two reference states. In this case the filter system can be switched into at least six different composite states.

In a set of embodiments, the gas sensor is further configured to determine, and the method further comprises determining that light received during the second composite state (first reference state, second measurement state) has been attenuated differently than light received during the third composite state (second reference state, first measurement state). The different attenuation may result from a different spectral distribution of light associated with the second composite state compared with the third composite state. This embodiment further ameliorates the ability of the gas sensor to distinguish between the target gas and a contaminant.

In a preferred set of embodiments, the contaminant is or comprises water. As discussed above, the absorption spectrum of water varies with the wavelength. In particular in such embodiments, the first and second reference wavelength profiles may be selected such that one of said wavelength profiles overlaps to a greater degree with the absorption spectrum of water than does the other reference wavelength profile. Thanks to this embodiment the gas sensor can even better detect the presence of water on a rigid object or gas or dust in the light path, in particular water on an optical object. The gas sensor can even more reliable distinguish between the attenuation caused by water and attenuation caused by the or one target gas. This feature further reduces the number of false alarms. The optional heating element needs only to be activated if really needed, i.e. if water or a further contaminant is detected.

In a set of embodiments, the first and second filters are arranged on the adaptable filter system in respective regions having respective first and second envelopes, wherein the first and second envelopes overlap. This may advantageously allow the radiation to be directed onto both of the first and second filters by arranging the light source such that the radiation is directed onto the first and second envelopes, e.g. the region of overlap.

In a set of embodiments, the first and second filters comprise respective first and second sets of filter elements. This allows filter elements from the same set to be arranged separately on the adaptable filter system while still being operated together (i.e. switching between their respective measurement and reference states in unison) so that each filter set functions as a single filter. This is advantageous as filter elements from the first set may be placed adjacent to filter elements from the second set, e.g. the first and second set of filter elements may be interspersed or interlaced. This provides the advantage of allowing more uniformity in the illumination of the first and second set of filter elements by the gas sensor light. Thereby the wavelength shape of composite states is less affected by non-uniform illumination. Preferably the first and second sets of filter elements are interspersed or interlaced.

Although the benefits of the invention may be achieved using only two different filters, the invention is not limited to two filters. The adaptable filter system may comprise a plurality (N>=2) of filters wherein every filter can be switched between a measurement state and at least one reference state independently from every other filter. Thereby the adaptable filter system can be switched between at least 2N composite states. Preferably up to N different reference wavelength profiles are used such that the target gas can be distinguished from up to N different contaminants. This may provide the advantage, for example, of allowing the gas sensor to distinguish between a target gas and a variety of contaminants having significantly different absorption spectra. For example, this may be achieved by providing respective reference states of the N filters where the reference state of each filter is different from the reference state of each other filter. As another example, this may be achieved by providing respective measurement states of the N filters where the measurement state of each filter is different from the measurement state of each other filter. It is also possible to use up to N different measurement wavelength profiles such that up to N or even more than N different target gases can be detected and distinguished form each other and from a contaminant.

In a set of embodiments, the first and second filters are micro-electromechanical (MEMS) filters. Where the first and second filters comprise respective first and second sets of filter elements, the filter elements may each be individual micro-electromechanical filter elements. Micro-electromechanical filters are advantageous as they can be precisely manufactured to produce the desired reference and measurement wavelength profiles. They can also be configured to switch rapidly between the wavelength profiles and have a small size which is helpful in arranging the filters so that they can be uniformly illuminated by the gas sensor light. The first and second filters may comprise respective sets of suspended micromechanical elements that are moveable vertically or angularly, preferably by electrostatic actuation. This provides a straightforward way to switch the filters, namely actuating them by applying suitable voltage signals. Where the first and second filters comprise respective sets of filter elements, the filter elements in each set may be connected electrically so that a respective voltage can be applied to each set.

The first and second filters may comprise diffractive optical elements. The wavelength profiles of the reference and measurement states may thus be achieved through diffraction of the incident light, e.g. a portion of the light may be diffracted so that the wavelength components desired for a wavelength profile are directed through the gas sensor to impinge on the detector.

According to the invention the gas sensor switches the adaptive filter system between at least three composite states. This is done by switching the first and second filters between the measurement and the reference state. A preferred frequency for switching a filter between the at least two states is between 100 Hz and 10,000 Hz, preferably between 500 Hz and 1,500 Hz, in particular about 1,000 Hz. Using a high switching frequency reduces the effect or impact which external factors may have on the comparison of the composite states, in particular effects due to temperature drifts. A too high frequency may damage a filter.

In a set of embodiments, the gas sensor may be configured to switch the first filter using a first input signal and to switch the second filter using a second input signal wherein the first input signal is a first square wave having a first frequency and the second input signal is a second square wave having a second frequency which is preferably double the first frequency. For example, the input signals may be applied voltages. Switching the filters using such square wave signals advantageously allows the filters to cycle through the possible permutations of reference and measurement states to cycle through the at least four composite states of the filter. However, it is not essential for the second frequency to be double the first frequency. The first and second signals may be synchronized with the second frequency being different from the first frequency. In this way, it is possible cycle through the possible permutations or a subset thereof (e.g. through three composite states).

In a set of embodiments, the gas sensor can be selectively operated in a detecting mode and in a distinguishing mode. In the detecting mode the gas sensor can detect the occurrence of the or one target gas or the contaminant (suspicious event) but cannot necessarily distinguish between target gas and contaminant. In the distinguishing mode the gas sensor can distinguish between target gas and contaminant. In the detecting mode the filter system is only switched between two composite states, preferably between the first composite state (both filters in the respective reference state) and the fourth composite state (both filters in the respective measurement state), i.e. such that the adaptable filter system is entirely in a reference state or entirely in a measurement state. If the gas sensor operated in the detecting mode detects the suspicious event, i.e. it obtains a positive signal, the gas sensor is switched into the distinguishing mode in which it is switched between at least three composite states.

Operating the gas sensor in the detecting mode and only in the distinguishing mode after obtaining a positive signal (attenuation) saves in many cases electrical energy, in particular if the energy or processing power used in the detecting mode is less than the energy or processing power used in the distinguishing mode. In general, it is not necessary to switch on the heating element as long as the gas sensor is operated in the detecting mode. A positive signal in the detecting mode triggers the step that the gas sensor is switched into the detecting mode. The or one heating element needs only to be switched on if the measurement result in the distinguishing mode is not reliable enough. This embodiment saves time compared with a conventional gas sensor only providing a detecting mode.

In a set of embodiments, the first and second filters may be switched using synchronized input signals of the same frequency, and then subsequently switched using the first and second square wave input signals. This has the effect of operating the sensor initially in the detecting mode in which only two composite states are used, followed by operating in the distinguishing mode in which at least three of the composite states are used. For example, the synchronized input signals in the detecting mode may cause the first and second filters to switch between the first and fourth composite states, i.e. such that the adaptable filter system is entirely in a reference state or entirely in a measurement state. In this detecting mode a gas may be detected but it is not possible to distinguish between a contaminant and a target gas, but subsequently switching (e.g. based on a possible positive signal) to the distinguishing mode comprises the use of at least three composite states to distinguish the contaminant from a target gas, as described above. This may be advantageous, for example, if the energy or processing power used in the detecting mode is less than the energy or processing power used in the distinguishing mode. Using a detecting mode initially and then switching to a distinguishing mode upon detecting a potential positive signal may thus improve the overall power efficiency of the gas sensor. The gas sensor may be configured to switch from a detecting mode to a distinguishing mode based on a possible positive signal. In addition, or as an alternative, the gas sensor may be configured to switch from a detecting mode to a distinguishing mode on a routine basis (e.g. on a regular basis), or when the detected gas concentration is above a threshold value. Performing such a regular or threshold check may be useful in implementations that monitor for unexpectedly high gas concentrations where a constant low level of gas is expected.

In one embodiment all four composite states have the same duration. In an alternative embodiment at least two composite states have different durations. In one implementation the duration of a composite state is achieved by adapting the duty cycle of the square pulse mentioned above. It may save energy when composite states are activated for different durations.

In a set of embodiments, the adaptable filter focuses the light. For example, the adaptable filter system may reflect the light, e.g. by having a structure that provides the function of a concave mirror. The adaptable filter system may comprise a transparent lens that focuses the light, e.g. a Fresnel lens. This may be advantageous as the adaptable filter system may thereby have a dual function of selecting wavelength profiles as well as focusing the light, e.g. through a measurement volume or onto the detector, thus reducing the complexity of the gas sensor by avoiding the need for an additional focusing component. The adaptable filter may also homogenize the emitted light, i.e. reduces the spatial variation of the light intensity.

In one embodiment the position of the light source is fixed with respect to the detector and the measurement volume. In one implementation of this embodiment the light source, the detector, the measurement volume, and the filter system are arranged in one common housing. In a preferred implementation of this embodiment the light source, the detector, and the filter system are arranged in a sensor housing and the measurement volume is arranged in a separate housing chamber with at least one aperture. The sensor housing is arranged adjacent to the measuring chamber and a transparent window between the sensor housing and the measuring element allows a light beam to enter and/or to leave the measuring chamber.

In a further embodiment the light source position can be changed with respect to the detector position. This embodiment enables to adapt the gas sensor to an environment (open path application), e.g. to the shape of a production plant. The light source may be arranged in a sender housing and the detector and the filter system in a receiver housing spaced apart from the sender housing. The position of the sender housing with respect to the receiver housing can be changed.

In one embodiment the gas sensor comprises one detector. It is also possible that the gas sensor comprises at least two detectors. Preferably the or at least two detectors use the same adaptable filter system with at least two filters and at least four composite states. It is possible to position the two detectors with a distance to each other. As the wavelength profile depends on the positioning of the detector relative to the filter system, the embodiment with at least two detectors helps to adapt the gas sensor to at least one target gas. It is also possible to place one detector adjacent to the other sensor. This embodiment may help to detect at least two different target gases.

In one embodiment the position of the or at least one detector with respect to the filter system is fixed. In an alternative embodiment the position of the or one detector with respect to the filter system can be changed. The wavelength profile achieved by the detector depends on the relative position. The embodiment with the moveable detector makes it possible to adjust or calibrate the detector to a given contaminant and/or a given target gas with a given wavelength profile. It is possible to adjust or calibrate the detector on a regular basis. Thereby drifts in a property of the filter system or the light source or the detector can at least partly be compensated.

The gas sensor may comprise one or more signal processors configured to process the detector signals to determine the presence of the contaminant in the gas sensor. However, it will be appreciated that it is not essential for processing of the signals to be carried out on board the gas sensor. For example, processing could be carried out remotely, for example at a node or server to which the gas sensor is communicatively linked. However, it may be advantageous for processing to be carried out on board the gas sensor as this obviates the need for transmission of data back and forth to a node or server, which may help to produce faster and/or more efficient output of gas sensing results.

One or more of the method steps described above may, where applicable, be carried out by the one or more processors. For example, the processing of the signals and controlling of the filter and/or a heating element may be carried out by the one or more processors.

Certain preferred embodiments will now be described, by way of example only, with reference to the accompanying drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 5 is graphs showing how the measurement and reference states of the first and second filter elements are combined to produce four composite states;

DESCRIPTION OF PREFERRED EMBODIMENTS

Figure 1:
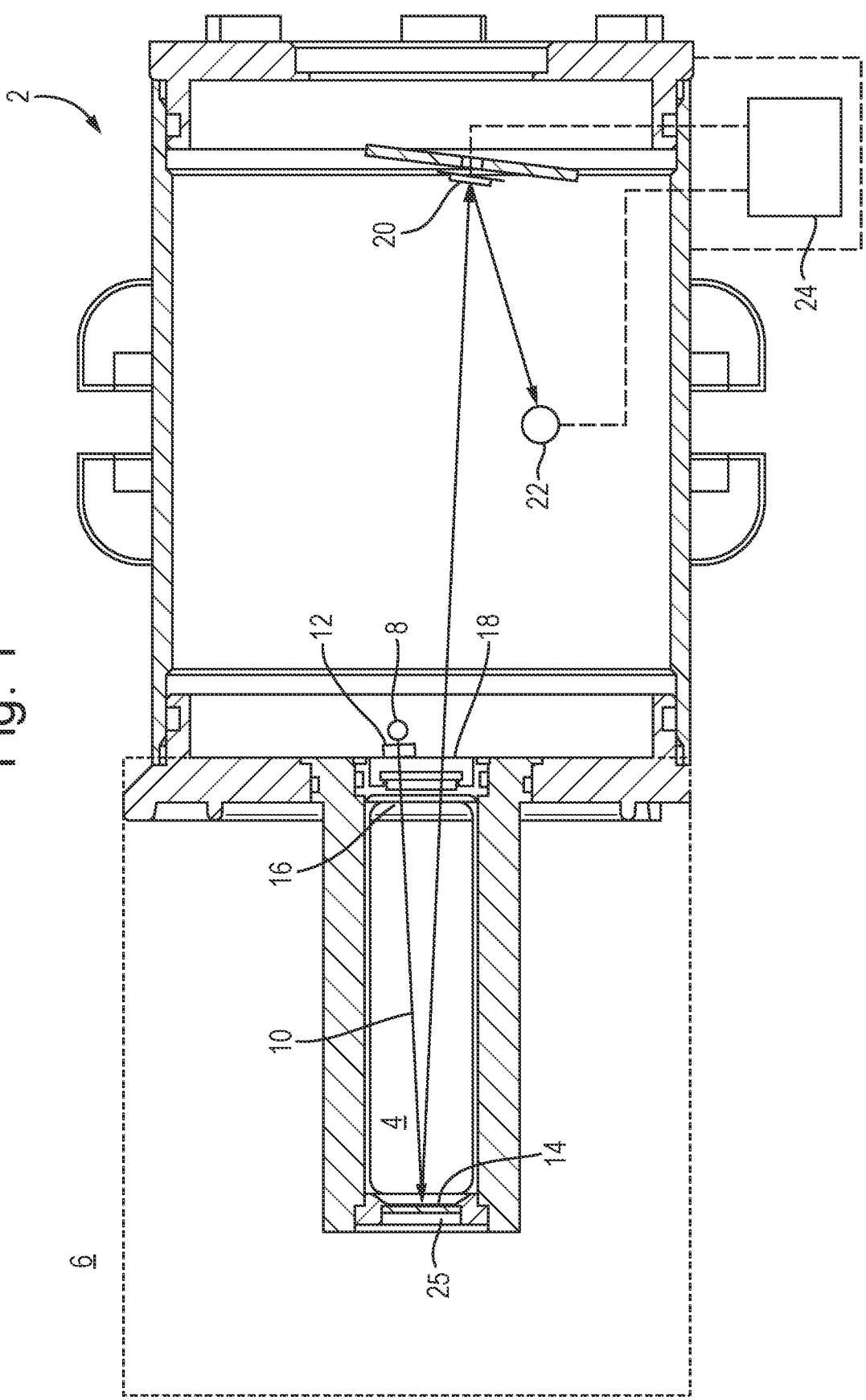
FIG. 1 is a sectional view showing an embodiment of a gas sensor in accordance with the present invention.

Referring to the drawings, FIG. 1 shows an embodiment of a gas sensor 2 in accordance with the present invention with a sensor housing and a separate housing for the measurement volume. The gas sensor comprises a measurement volume 4 into which air from the gas sensor's surroundings 6 can enter via holes (not shown) connecting the interior of the measurement volume with the gas sensor's exterior environment and can leave the interior through the holes. The gas sensor 2 comprises a light source 8 for producing light. A light beam represented by a light path 10 is generated by the light source 8 and is directed by optical components including a lens 12 into the measurement volume 4. In the measurement volume 4, the light beam 10 passes through the air that is being tested for at least one target gas, and then is reflected by a mirror 14 back through the measurement volume 4. The light beam 10 passes through a window 16 and an aperture 18 after which it impinges on an adaptive filter system implemented as a micro-electromechanical structure (MEMS) filter system 20. The MEMS filter system 20 is discussed in more detail below with reference to the subsequent Figures. In addition to filtering the light, the MEMS filter 20 also reflects and focuses the light onto photo detector 22 where the light is detected. The light source 8, the lens 12, the mirror 14, the window 16, the filter system 20, and the detector 22 are arranged in a sensing housing. The aperture 18 is arranged in a wall of the sensing housing and overlaps with the window 16. It is also possible that the window 16 serves as the aperture 18.

In a possible implementation (not shown) the light source 8, the aperture 18, the filter system 20, and the detector 22 may be attached to the same substrate and are in the same plane. A second mirror reflects the light from the aperture 18 to the MEMS filter system 20. This embodiment may save space.

The MEMS filter system 20 and the photo detector 22 are connected to one or more processors, indicated schematically by a box 24. The processors process the signals from the photo detector 22 to determine the presence of a target gas or a contaminant, in particular water. The processors also control the operation of the MEMS filter 20. A heating element 25 is provided on the back of the mirror 14. Additional heating elements may be provided on other optical elements. The heating element(s) may be activated to remove condensation if water is detected in the gas sensor.

Figure 2:
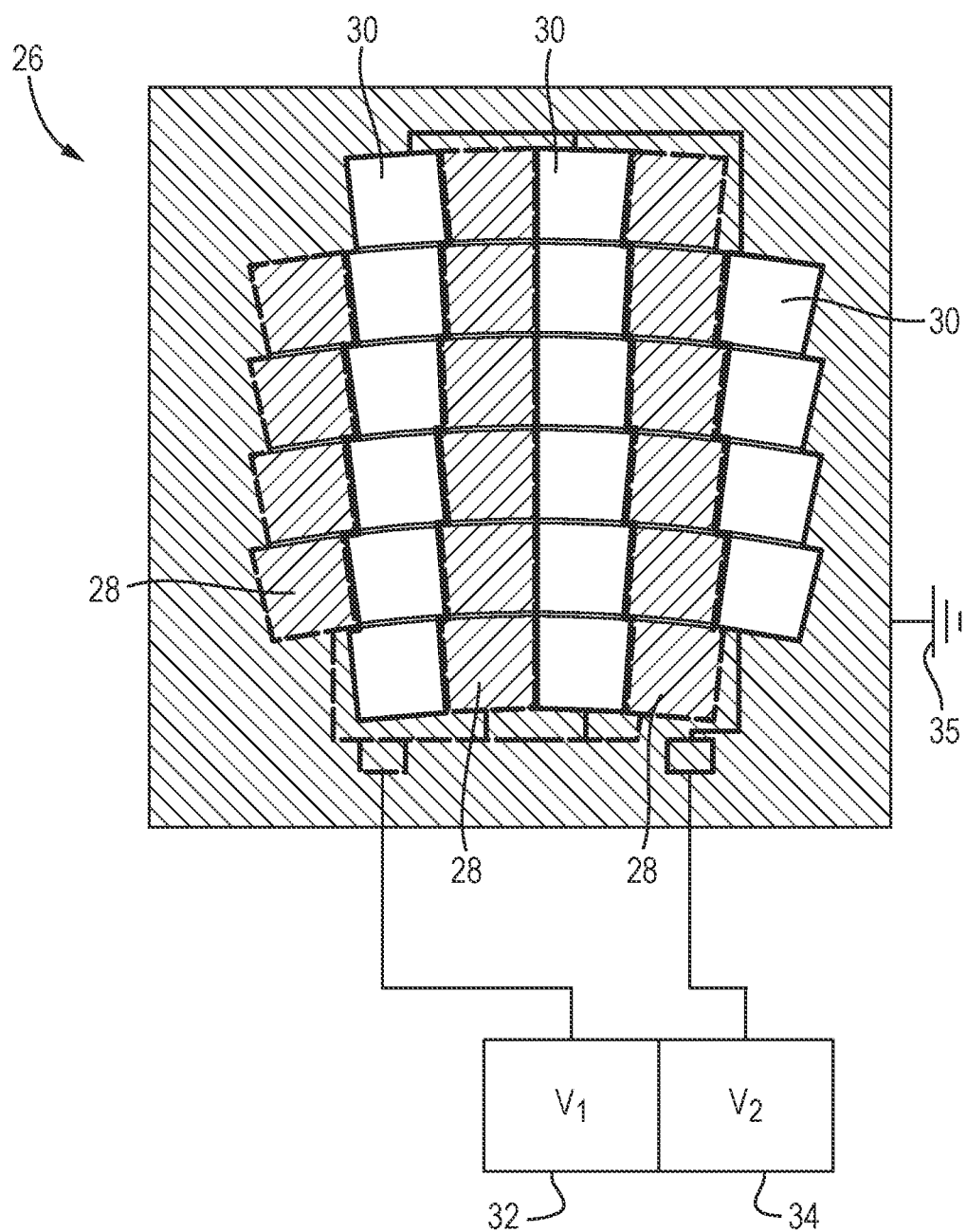
FIG. 2 is a schematic view of an adaptable filter system in accordance with an embodiment of the present invention.

FIG. 2 shows an adaptable MEMS filter system 26 in accordance with an embodiment of the present invention. The MEMS filter 26 comprises a first group of first filter elements 28 and a second group of second filter elements 30. The first filter elements 28 and the second filter elements 30 are interlaced in that they are provided in columns which alternate between the first and second filter elements 28, 30. This arrangement of the filter elements 28, 30 is preferred but not essential. The filter elements 28, 30 need not be interlaced, or they may be interspersed or interlaced in a different way, e.g. alternating rows or a chequerboard pattern.

The first filter elements 28 and the second filter elements 30 are connected to respective first and second voltage sources 32, 34. The first voltage source 32 applies a voltage signal V1 to the first filter elements 28. The second voltage source 34 applies a second voltage signal V2 to the second filter elements.

Each filter element is or comprises a micro-electromechanical system (MEMS) actuator which can be switched between a reference state and a measurement state by applying different voltages to it, as described below with reference to FIGS. 3A and 3B. Preferably the voltages are of the same magnitude but have different frequencies and/or different duty cycles.

Some parts of the filter system 20 are electrically isolated from the filters 28 and 30 and are connected to ground what is shown by the earthing (ground) 35.

Figure 3A:
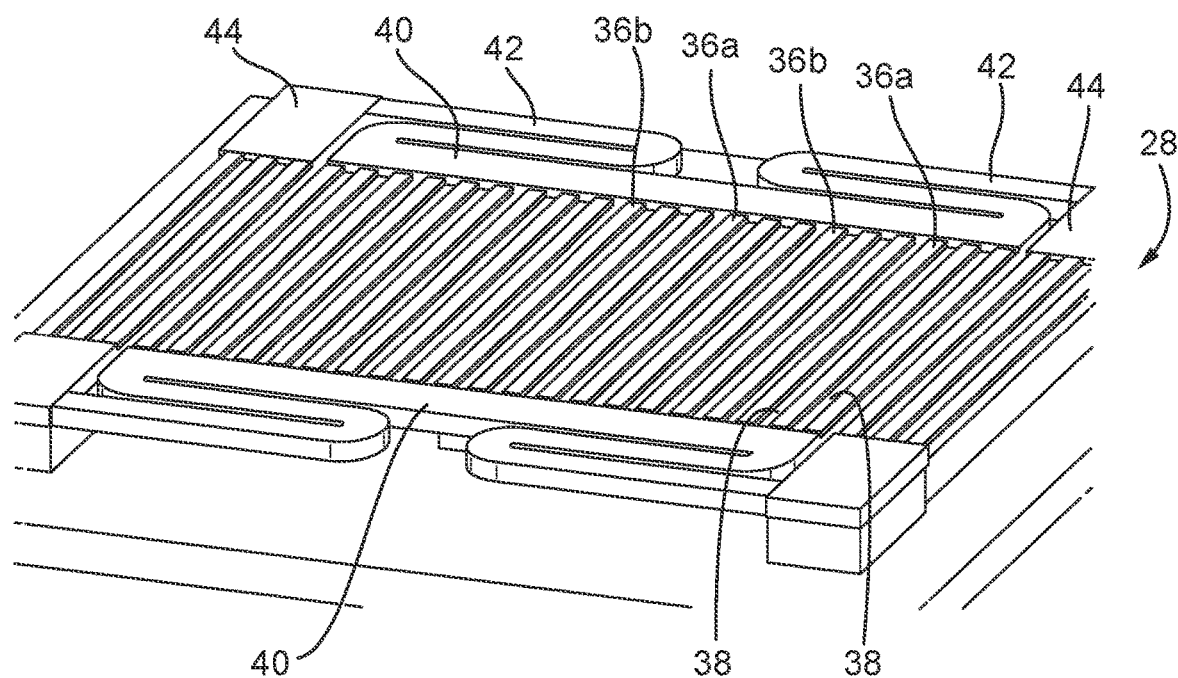
FIG. 3A is a perspective view of a first filter element of the filter system of FIG. 2, wherein the filter element is in its measurement state.

FIG. 3A shows an example of a first filter element 28 in a measurement state. The other elements in the set of first filter elements 28 have a similar structure and function. Each of the second filter elements 30 may have a similar (although not identical) structure to that of the first filter elements 28.

The first filter element 28 comprises two alternating sets of slats 36a, 36b. Each slat 36a, 36b comprises diffraction grooves 38 so that it behaves as a diffraction grating. The two sets of slats are independent of each other so that each slat 36a can move relative to its neighbor 36b from the other set. The slats 36a of one set are connected to a support beam 40 at the respective ends of each slat 36a. The support beams 40 are connected by flexible arms 42 to a main support 44. The slats 36b of the other set are supported on respective mounts 44 (visible in FIG. 3B) underneath each slat 36b.

FIG. 3A shows the filter element 28 in its relaxed state, in which no voltage is applied. When no voltage is applied, the flexible arms 42 are relaxed, and the two sets of slats 36a, 36b all lie in the same plane. When light impinges on the filter in this state, the composite structure of the slats 36a, 36b diffract the light to filter it. In this state, the filter passes radiation falling within a band of frequencies having the form of a single peak centered on a wavelength falling within an absorption band of a target gas.

Figure 3B:
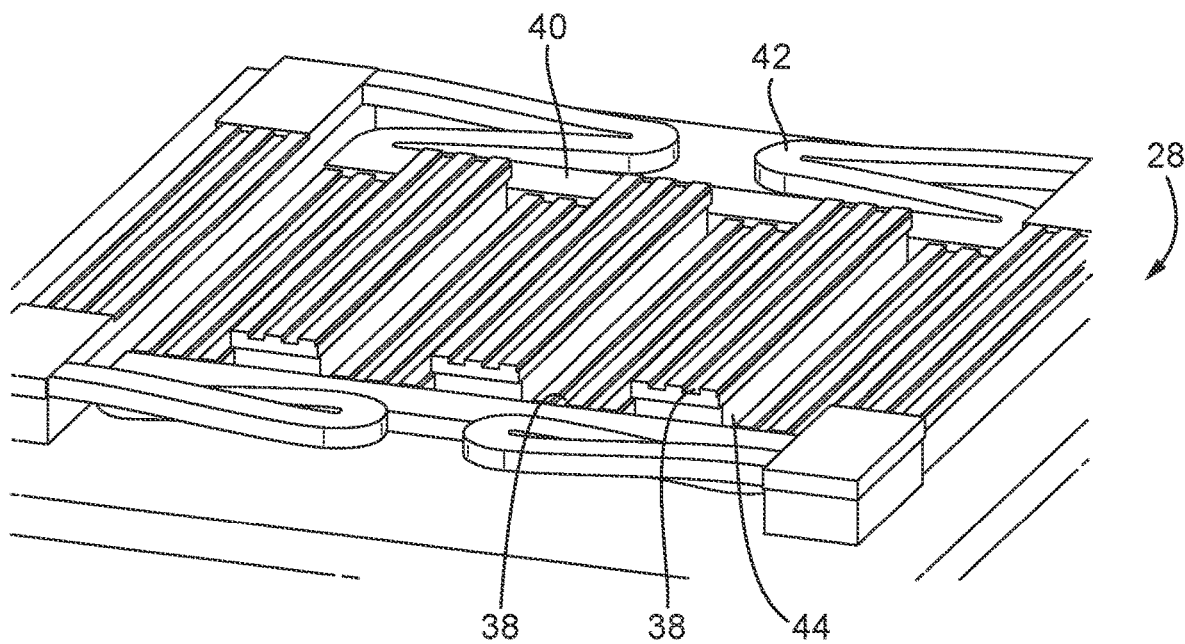
FIG. 3B is a perspective view of the filter element of FIG. 3A in its reference state.

FIG. 3B shows the filter 28 in its actuated state, i.e. with a voltage applied, which corresponds to its reference state. Above a threshold voltage value, one set of slats 36a is displaced downwards with respect to the other set of slats 36b (i.e. perpendicular to the plane of the filter element surface). This movement is permitted by the support 40 and flexible arms 42 due to flexing of the arms 42.

In this reference state, the light incident on the filter is diffracted by the grooves 38 to produce two side band peaks either side of the central frequency of the single peak of the measurement state. The vertical displacement of the slats 36a in a reference state provides separation of the slats corresponding to a quarter of a wavelength optical path difference, so that the light is directed into the first diffractive order, i.e. the sidebands.

Figure 4A:
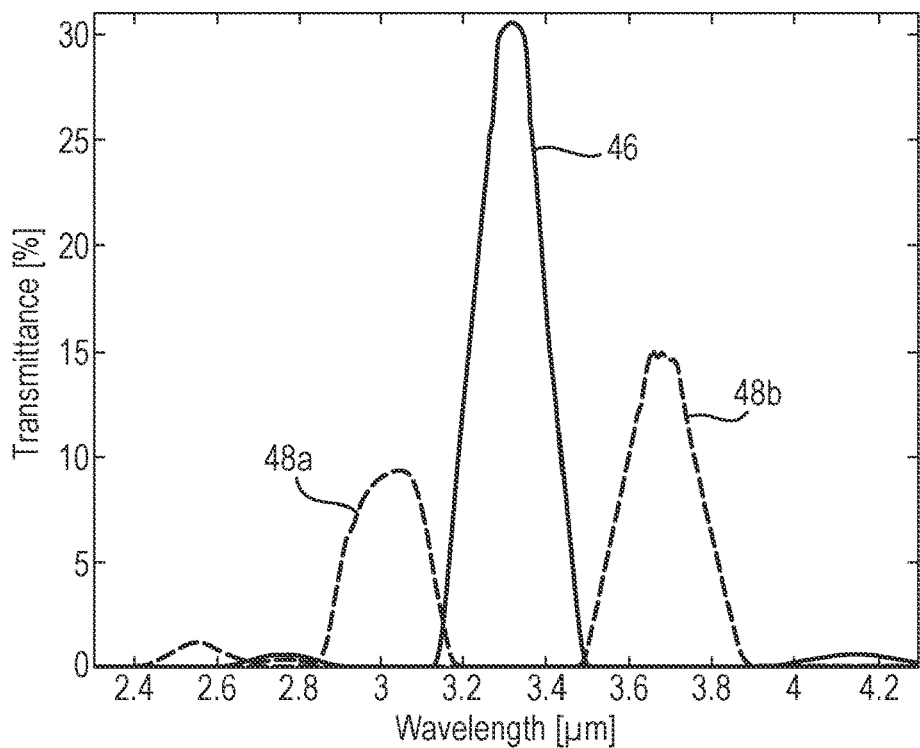
FIG. 4A is a graph showing the wavelength transmittance profiles of the measurement and reference states for the first filter elements of FIG. 2.

FIG. 4A shows the wavelength transmittance profiles of the measurement and reference states for the first filter elements 28. In the measurement state, a single central peak 46 is produced. This means that the filter only passes radiation falling within the wavelength range of the peak, i.e., in this example, approximately 3.15 μm to 3.5 μm. There may be some transmittance outside of this range, but it will typically be negligible and can be blocked, e.g. using a bandpass filter.

In the reference state, the transmittance profile shows two side bands 48a, 48b either side of central peak 46 of the measurement state. This means that in the reference state, the filter element 28 passes virtually no radiation falling in the central range of wavelengths corresponding to the measurement peak 46 but transmits a significant amount of radiation in the ranges either side of this peak, i.e. approximately 2.85 μm to 3.15 μm and 3.5 μm to 3.9 μm. As can be seen the side band 48a at shorter wavelengths is smaller, i.e. has a smaller area under the peak, than the side band at longer wavelengths 48b. This means that the filter 28 in the reference state passes more radiation at long wavelengths than at short wavelengths.

Figure 4B:
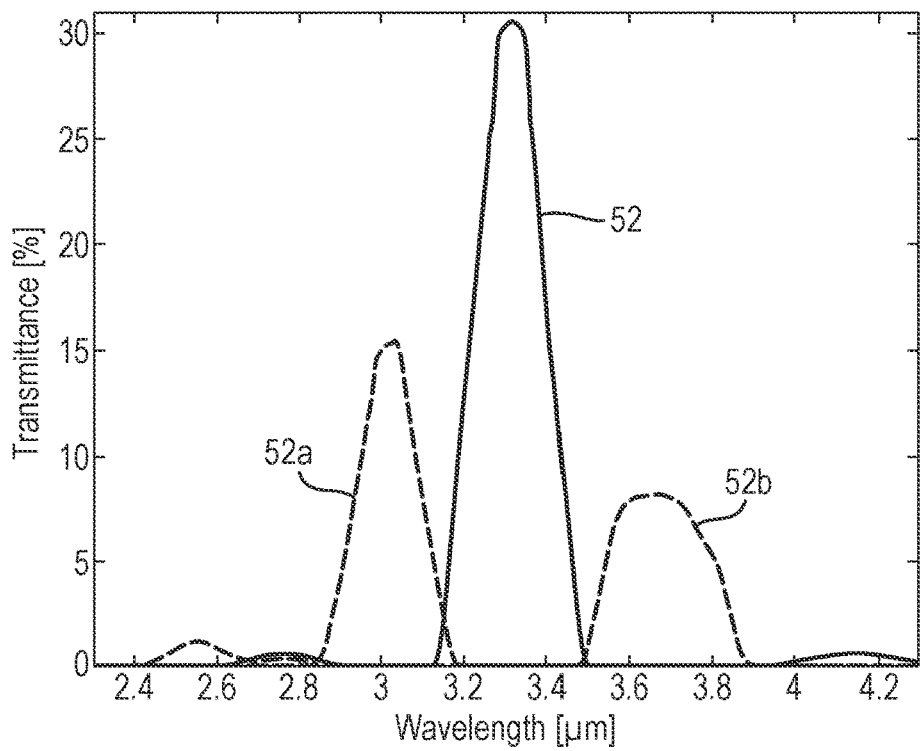
FIG. 4B is a graph showing the wavelength transmittance profiles for the second filter elements of in FIG. 2.

FIG. 4B shows corresponding wavelength transmittance profiles for the second filter elements 30 of in FIG. 2. As noted above, the second filter elements 30 operate between a measurement state and a reference state in the same manner as shown in FIGS. 3A and 3B, but the grating line profile of the second filter elements 30 is different from that of the first filter elements 28, which creates a different transmittance profile for the reference state compared with that of the first filter elements 28.

As can be seen in FIG. 4B, there is a central peak 52 in the measurement state. The central peak 52 has the same profile as the measurement state peak 46 of the first filter element 28 shown in FIG. 4A. However, in the reference state, there are two side bands 52a and 52b, where the side band 52b at longer wavelengths is smaller than the side band 52a at shorter wavelengths. This means that in the reference state, the second filter elements 30 transmit more radiation at short wavelengths than at long wavelengths, i.e. the opposite of the first filter elements 28.

FIG. 5 shows how the measurement and reference states of the first and second filter elements are combined to produce four composite states. The first filter's measurement state contains a single peak 54, and the first filter's reference state contains asymmetric side band peaks 56a and 56b. Similarly, the second filter's measurement state contains a single peak 58 and the second filter's reference state contains asymmetric side band peaks 60a and 60b.

As the first and second filter elements, 28, 30, each have two independent states, the measurement and reference states, there are four different combinations of the states, which produce four composite states.

In a first composite state (S11), the first and second filter elements 28, 30 are activated, i.e. they are in their respective reference states. The combination of the two reference states produces two symmetric side band peaks 62, which correspond to the combination of the asymmetric side band peaks 56a, 60a, 56b, 60b.

In a second composite state (S10), the first filter elements 28 are in the active or reference state, while the second filter elements 30 are in the rest or measurement state. This combination produces the asymmetric side bands 64 and a small central peak 66. These asymmetric side bands 64 and small central peak 66 correspond to the combination of the side band peaks 56a and 56b with the central peak 58.

In a third composite state (S01), the first filter elements 28 are in the measurement state and the second filter elements 30 are in the reference state. This combination produces asymmetric side band peaks 68 and a small central peak 66. The central peak 66 and asymmetric side band peaks 68 correspond to the combination of the side band peaks 60a and 60b with the central peak 54.

In a fourth composite state (S00), the first filter elements 28 and the second filter elements 30 are in the measurement state. This is represented by the large central peak 70, which represents the combination of the central peaks 54 and 58.

Figure 6:
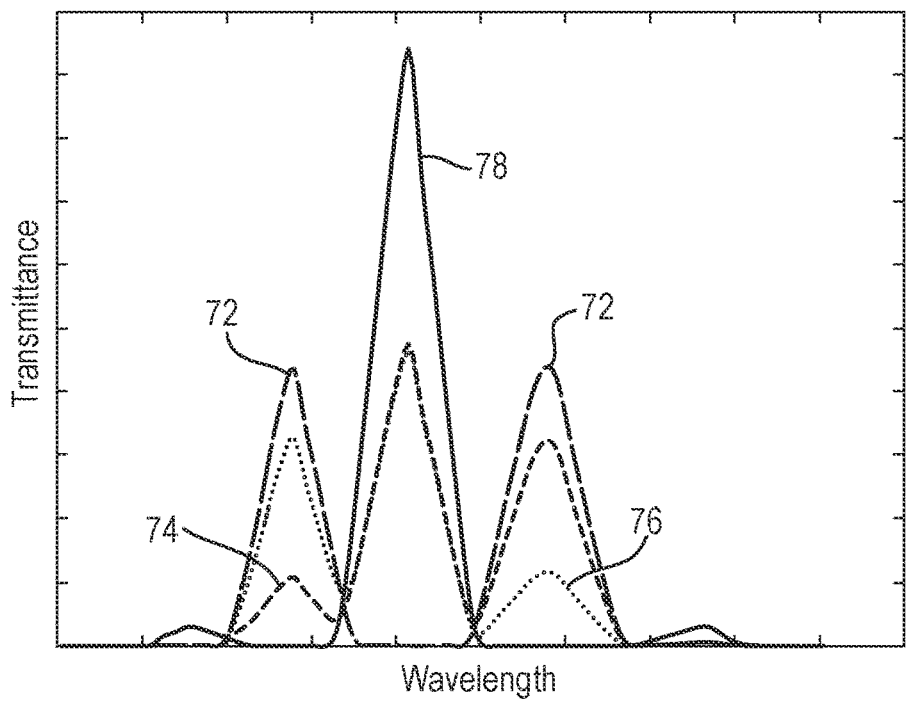
FIG. 6 is a graph showing examples of transmittance wavelength profiles for four composite states.

FIG. 6 shows examples of transmittance wavelength profiles for these four composite states. The two equal side bands 72 correspond to the first composite state (S11, i.e. both sets of filter elements in reference state). The asymmetric transmittance wavelength profile 74, which has lower transmittance at shorter wavelengths, corresponds to the second composite state (S10, i.e. first filter elements in the reference state and second filter elements in the measurement state). The other asymmetric wave length transmittance profile 76, which has higher transmittance at short wavelengths, corresponds to the third composite state (S01, i.e. first filter elements in the measurement state and second filter elements in the reference state). The large central peak 78 corresponds to the fourth composite state (S00, i.e. both sets of filter elements in the measurement state).

Figure 7:
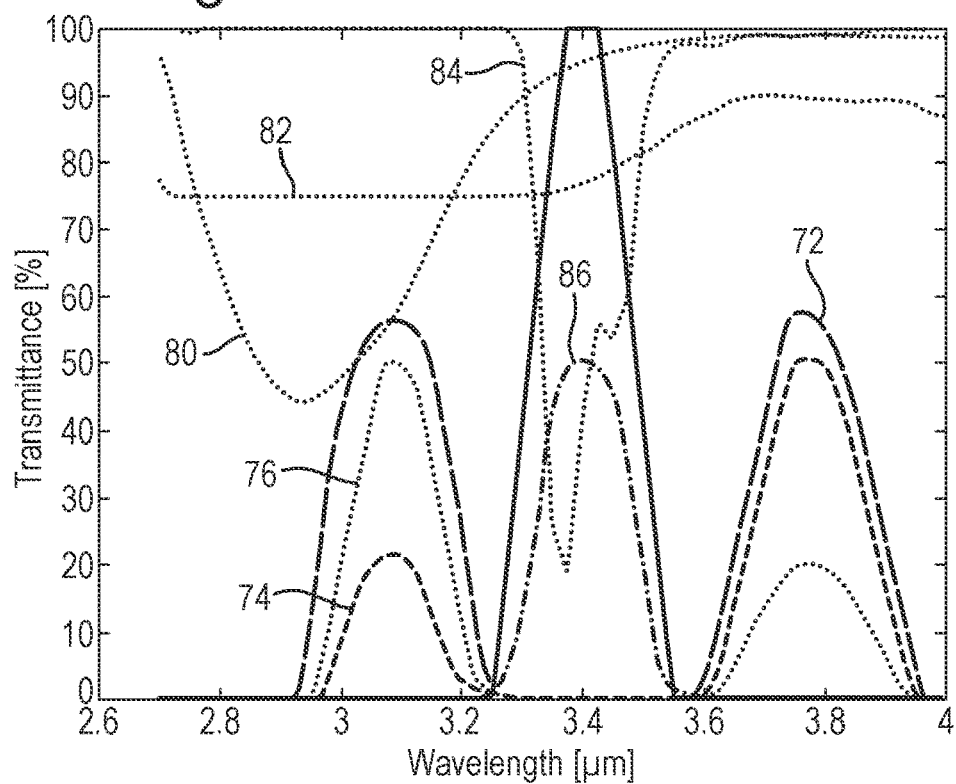
FIG. 7 is a graph showing the transmittance profiles of FIG. 6 overlaid on the transmittance profiles for water and a target gas.

FIG. 7 shows the transmittance profiles of FIG. 6 overlaid on the transmittance profiles for water and a target gas. In this example, the target gas is propane, but the invention can be used for detecting other gases, including but not limited to other hydrocarbon gases. The transmittance profile for a water film on one or more optical element in the gas sensor is shown by a line 80. As can be seen a film of water on one or more optical elements absorbs strongly at shorter wavelengths, overlapping with the shorter wavelength sideband peaks of the composite states, but there is very little absorption in the wavelength range corresponding to the central measurement peaks or the longer wavelength sideband peaks.

The transmittance profile of water droplets in the gas sensor is shown by a second line 82. As can be seen water droplets absorb slightly more strongly in shorter to mid-range wavelengths, i.e. overlapping with the shorter wavelength sidebands and measurement peaks but absorb less strongly at longer wavelengths corresponding to the longer wavelength side bands.

The transmittance profile for the target gas, propane, is shown by another line 84. As can be seen propane absorbs very strongly in the wavelengths corresponding to the central peaks (and the central frequency of the measurement state peaks is selected for this reason). Radiation corresponding to the fourth composite state would therefore be attenuated in the presence of a target gas. However, there is virtually no absorption by the target gas at the wavelengths corresponding to the sideband peaks present in the other composite states.

It can thus be seen that in the presence of water droplets or a water film, there will be greater absorption at shorter wavelengths than at longer wavelengths. As a result, radiation that has been filtered by the third composite state profile 76 (dotted line) will be attenuated to a greater extent than radiation filtered by the second composite state profile 74 (short dashed line), because the former portion of radiation contains proportionately more radiation at short wavelengths.

In contrast, in the presence of the target gas, which has negligible absorption in the wavelength ranges of both sidebands, the second and third composite states will be affected equally, notwithstanding their different wavelength distribution of radiation, because there is virtually no absorption of the sidebands at all. There will be absorption in the wavelength range of the central peak of each of the second and third composite states, but as the central peak of the second and third states is the same, they will be affected equally by a target gas.

Radiation filtered by the filter in its first composite state 72 (both filters in reference state, long dashed line) would be largely unaffected by the presence of a target gas, because there is virtually no overlap between the side bands 72 of the first state and range at which the target gas absorbs radiation.

It can thus be seen that in the presence of water, the second and third composite state radiation is affected differently for each state, whereas in the presence of a target gas, the second and third composite state radiation is affected by the same amount. It is thus possible to distinguish between water and the presence of a target gas according to whether or not the second and third composite state radiation is attenuated by the same or different amounts.

Figure 8:
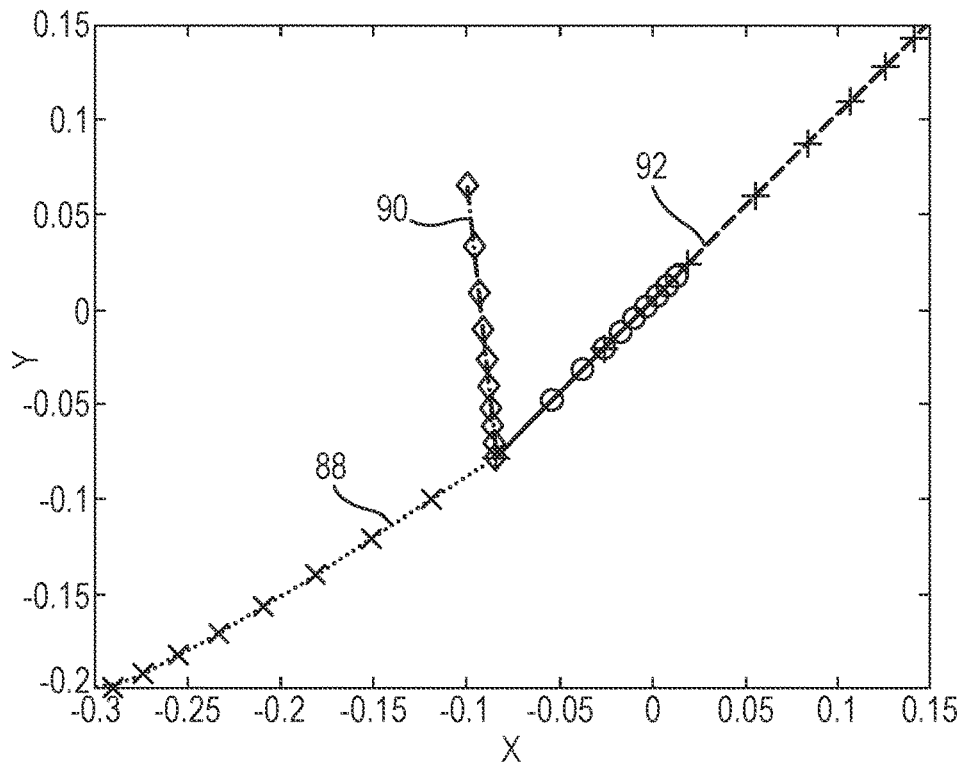
FIG. 8 is a graph showing the analysis of detected radiation to distinguish between water and a target gas.

FIG. 8 shows how the radiation intensity during the different composite states of the filter can be processed and analyzed to distinguish between water and a target gas. First, an example analysis method of the prior art is briefly described for comparison purposes.

In methods according to the prior art, in which only a single measurement state and a single reference state are used, the presence of a gas is assessed using the ratio of the measurement signal and the reference signal. e.g. the gas concentration c may be calculated based on the ratio of the measured light intensity in the reference state $I_{Ref}$ and the measured light intensity in the measurement state $I_{Meas}$ according to:

$$c = f(r), r = \frac{I_{Ref}}{I_{Meas}} - 1$$

where f is a non-linear and monotonous function. However, using only r, or similar functions of the ratio of $I_{Ref}$ and $I_{Meas}$, it is not possible to discriminate between reductions in $I_{Ref}$ and $I_{Meas}$ caused by gas and reductions caused by water. However, using the signals obtained using the four composite states, such discrimination is possible, as described below.

FIG. 8 shows a graph of signals y and x, where y and x are defined as:

$$x = 1 - \frac{I_{S10}}{I_{S11}}, y = 1 - \frac{I_{S01}}{I_{S11}}$$

$I_{S11}$, $I_{S10}$ and $I_{S01}$ are the radiation intensities measured in the first, second and third states (S11, S10 and S01) respectively. In this example, the first, second and third composite states are used, although it is in principle possible to carry out a similar analysis using three other composite states, e.g. the second, third and fourth composite states.

The calculation of the signal x effectively normalizes the second composite state against the first (i.e. combined reference) composite state, cancelling out the effect of any conditions in the gas sensor (such as dirty optics or a weak source) that may attenuate the radiation. These effects can be removed in this way because they affect the first and second states equally. Similarly, the signal y represents the normalization of the third state against the first state.

The normalized second and third state signals, expressed in terms of signals x and y, are then compared against each other to see if they have been attenuated by different amounts (indicating the presence of water) or by the same amount (indicating the presence of a target gas).

Signal y is plotted against signal x, as shown in FIG. 8 for data recorded using the gas sensor in the presence of water droplets, a water film on the gas sensor optical elements, and hydrocarbon gases (propane and methane). Owing to the different way that the radiation in the second and third composite states is affected by the presence of water compared with the presence of a target gas, the relationship between the signals x and y is different for a water film, water droplets, and a target gas.

As can be seen in FIG. 8, plotting the data in this way gives rise to three distinct arms in the graph. The first arm 88 corresponds to the presence of a water film. The second arm 90 corresponds to the presence of water droplets, and the third arm 92 corresponds to the presence of a hydrocarbon gas.

Accordingly, by conducting such an analysis of recorded radiation intensity for three composite states as measured by the gas sensor, e.g. carrying out such analysis using a processor in the gas sensor, it is possible to identify which of these three arms the recorded data points falls within, and thereby to distinguish between water and a target gas in the gas sensor.

As mentioned above, it may be advantageous under some circumstances to operate the gas sensor of the present invention in a detecting mode, which uses only two of the composite states, e.g. the first and fourth composite states. This detecting mode is described with reference to FIGS. 9 and 10.

Figure 9:
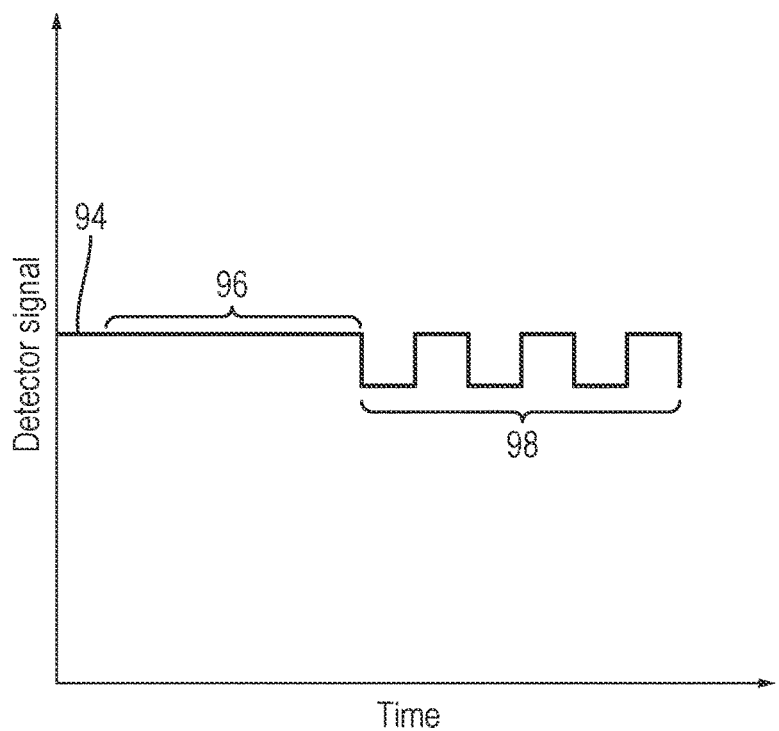
FIG. 9 is a graph showing a detector signal that may be obtained in a detecting mode of the gas sensor (using two composite states)

FIG. 9 shows a detector signal 94, plotted against time, that may be obtained in accordance with such a detecting mode operation. When operated in the detecting mode, the filter is switched alternately between the first (combined reference) composite state and the fourth (combined measurement) composite state. The measured signal therefore alternates between the intensity detected in the reference state and the intensity detected in the measurement state. When the reference state and measurement state intensities are different, this gives rise to a modulated signal. When the reference state and measurement state intensities are the same, the measured signal is flat.

As can be seen initially there is a portion 96 of the signal that is flat. This corresponds to there being no target gas present in the sensor measurement volume. As there is no gas present, there is no preferential absorption of the radiation of the fourth (combined measurement) composite state compared with the first (combined reference) composite state, and so the detected intensities are the same.

Subsequently, there is a portion 98 of the signal that has a modulated form. This corresponds to the potential presence of a target gas in the measurement volume. As noted previously, in the presence of a target gas, the fourth (measurement) state radiation is preferentially absorbed compared with the first (reference) state radiation, owing to the significant overlap between the measurement state peak and the absorption band of the target gas. As noted previously, a similar effect is seen in the presence of water. This preferential absorption in the fourth (measurement) state compared with the first (reference) state results in the observed modulation of the signal.

Figure 10:
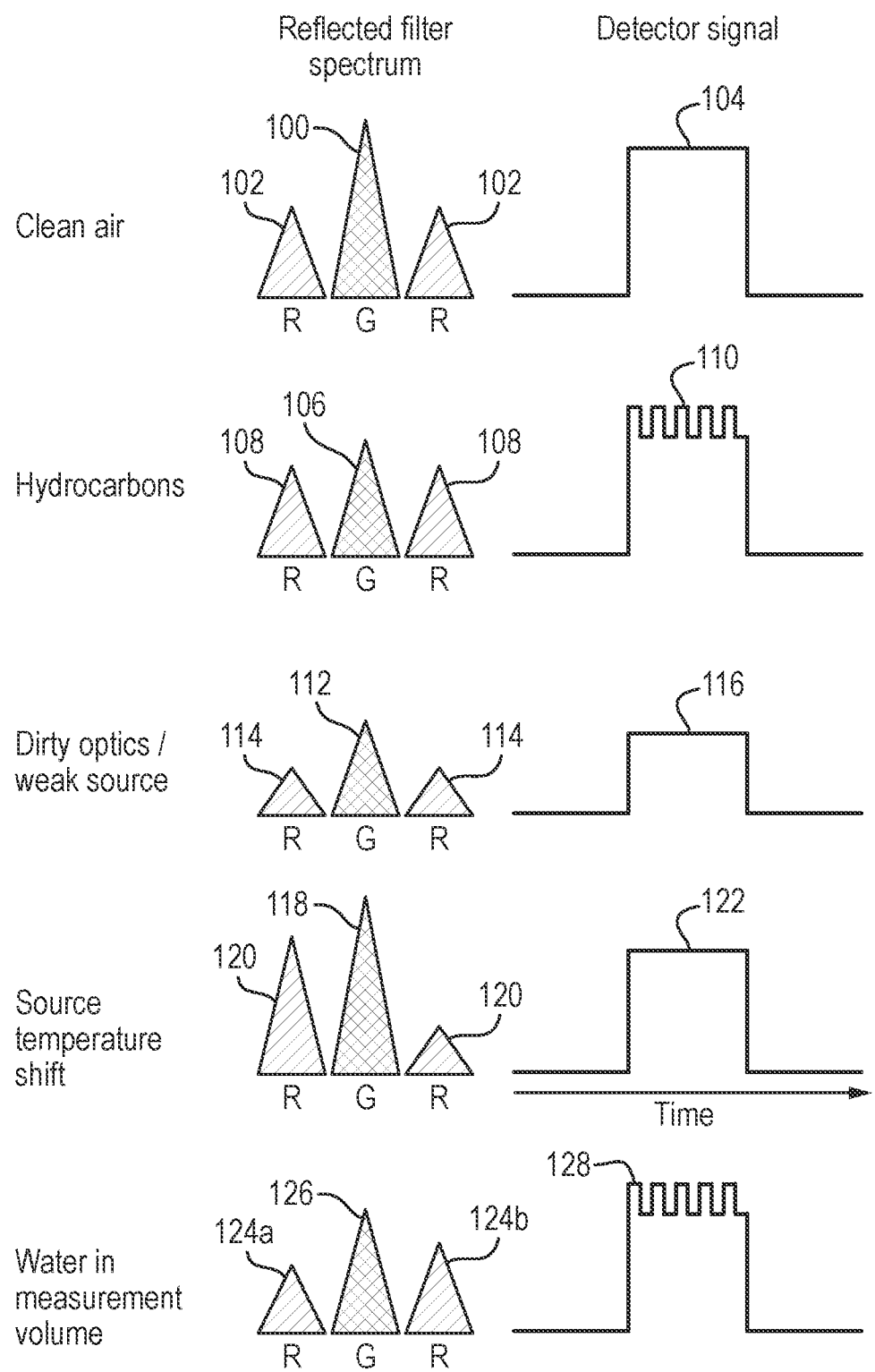
FIG. 10 shows how the use of a detecting mode can eliminate some potential sources of false alarms.

The detecting mode may be a useful way to eliminate some sources of error to identify a potentially genuine gas condition, which can then be investigated further by switching from the detecting mode to a distinguishing mode using at least three composite states (e.g. as described above with reference to FIGS. 8 to 9). FIG. 10 shows how the use of a detecting mode using only two states can eliminate some potential sources of false alarms.

In FIG. 10, there is a schematic representation of the measurement peak 100 and reference peaks 102 in the presence of clean air. No significant absorption is observed for the measurement peak or the reference peaks, and so the detector signal 104 is flat during the measurement. It becomes apparent that two reference sidebands increase the ability of the gas sensor to detect an event which may be the target gas or a contaminant (detecting mode). In many cases water as a contaminant will cause positive gas alarm.

In the presence of hydrocarbons, a reduced measurement peak 106 is observed, compared with reference sideband peaks 108 that are not substantially affected. Consequently, the total radiation corresponding to the measurement state is attenuated compared to the total radiation of the sidebands. This results in a measurement signal and a reference signal that are different from each other. As a result, the detector signal 110 has a modulated profile.

In the case of dirty optics, e.g. with dust or other particulate matter on the surface, such that some of the light is blocked, or a weak source where the intensity across the entire frequency spectrum is reduced, there is a reduction in the measurement peak 112 as well as the reference sidebands 114 by approximately the same amount. As the attenuation is roughly equal, the detector signal 116 is flat and there is no false alarm.

If there is a source temperature shift, this may result in a change in the wavelength distribution of the light from the source, but the ratio of the measurement band radiation 118 and the reference band radiation 120 will remain the same, again resulting in a flat signal 122.

However, in the presence of water, the reference band radiation 124a, 124b and the measurement band radiation 126 are attenuated by different amounts owing to the particular absorption spectrum of water. This gives rise to a modulated signal 128 similar to the detector signal 110 observed for hydrocarbons. In the case of water, one of the reference sidebands 124a is attenuated more than the other sideband 124b. However, in the detecting mode water cannot be distinguished from a target gas, because for both water and a target gas, all that is observed is that the total measurement state radiation and the total reference state radiation are different. Thus, the detection of a modulated signal may be used as a prompt to cause the gas sensor to switch from the detecting mode which uses only two composite states to a mode which uses at least three composite states, e.g. as described above with reference to FIGS. 1 to 8, to enable the gas sensor 2 to distinguish between a contaminant such as water and a target gas.

While specific embodiments of the invention have been shown and described in detail to illustrate the application of the principles of the invention, it will be understood that the invention may be embodied otherwise without departing from such principles.

REFERENCE SIGNS 2 gas sensor, comprises the light source 8, the measurement volume 4, the filter system 20, the detector 22, the optional mirror 14, the optional window 16, the optional aperture 18, the optional processors 24, and the optional heating element 25
4 measurement volume
8 light source
10 light path from the source 8 to the detector 22
12 lens
14 mirror
16 window
18 aperture
20 adaptive filter system, comprises the filters 28 and 30
22 photo detector
24 processors of the gas sensor 2
25 heating element
26 implementation of an adaptive MEMS filter system
28 first optical filter
30 second optical filter
32 first voltage source
34 second voltage source
35 earthing of the filter system 20
36a, 36b slats of the first filter element 28
38 grooves for diffracting light
40 support beams for the slats 36a
42 flexible arms for the support beams 44
44 main support
46 single central peak of the first measurement wavelength transmittance profile
48a, 48b side bands of the first reference wavelength transmittance profile
52 single central peak of the second measurement wavelength transmittance profile
52a, 52b side bands of the second reference wavelength transmittance profile
54 single peak of the first filter 28—measurement state
56a, 56b side bands of the first filter 28—reference state
58 single peak of the second filter 30—measurement state
60a, 60b side bands of the second filter 30—reference state
72 two equal side bands corresponding to the first composite state S11
74 asymmetric transmittance wavelength profile corresponding to the second composite state S10
76 asymmetric transmittance wavelength profile corresponding to the third composite state S01
78 large central peak corresponding to the fourth composite state S00
80 transmittance profile for a water film on an optical element
82 transmittance profile of water droplets
84 transmittance profile for the target gas
88 first arm in a graph corresponding to the presence of a water film
90 second arm in a graph corresponding to the presence of water droplets
92 third arm in a graph corresponding to the presence of a hydrocarbon gas
94 detector signal obtained in a detecting mode
96 flat portion of the detector signal 94
98 modulated portion of the detector signal 94
100 measurement peak in the presence of clean air
102 reference peaks in the presence of clean air
104 detector signal in the presence of clean air
106 reduced measurement peak in the presence of hydrocarbons
108 reference sideband peaks in the presence of hydrocarbons
110 detector signal in the presence of hydrocarbons
112 measurement peak in the case of dirty optics
114 reference sidebands in the case of dirty optics
116 detector signal in the case of dirty optics
118 measurement band radiation
120 reference band radiation
122 flat signal
124a, 124b reference band radiation in the presence of water
126 measurement band radiation in the presence of water
128 modulated detector signal in the presence of water
S11 first composite state—both filters 28, 30 in reference state
S10 second composite state—first filter 28 in reference state, second filter 30 in measurement state
S01 third composite state—first filter 28 in measurement state, second filter 30 in reference state
S00 fourth composite state—both filters 28, 30 in measurement state

The invention claimed is:

1. A gas sensor configured and arranged to detect at least one target gas, wherein the gas sensor comprises
a light source configured and arranged to emit light,
a measurement volume,
a detector configured and arranged to receive light, and
an adaptable filter system,
wherein the measurement volume and the adaptable filter system are disposed in a light path between the light source and the detector,
wherein the adaptable filter system comprises a first optical filter and a second optical filter,
wherein the first filter is operable to switch between
a first reference state in which the first filter passes light according to a first reference wavelength profile and
a first measurement state in which the first filter passes light according to a first measurement wavelength profile,
wherein the second filter is operable, independently of the first filter, to switch between
a second reference state in which the second filter passes light according to a second reference wavelength profile and
a second measurement state in which the second filter passes light according to a second measurement wavelength profile,
wherein the first reference wavelength profile is different from the second reference wavelength profile, the adaptable filter system thereby being switchable between at least four different composite states, the composite states comprising:
a first composite state in which the first filter is in the first reference state and the second filter is in the second reference state,
a second composite state in which the first filter is in the first reference state and the second filter is in the second measurement state,
a third composite state in which the first filter is in the first measurement state and the second filter is in the second reference state, and
a fourth composite state in which the first filter is in the first measurement state and the second filter is in the second measurement state,
wherein the gas sensor is configured to switch the adaptable filter system between at least three of the composite states,
wherein the detector is configured and arranged to generate one respective detector signal corresponding to light received by the detector for every one of the at least three of the composite states used, and
wherein the gas sensor is configured to determine a presence of a contaminant other than the target gas in the light path between the light source and the detector by comparing with each other the respective detector signals generated during the at least three of the composite states.

2. Gas sensor according to claim 1, wherein the gas sensor further comprises
at least one object which is arranged in the path of the light between the light source and the detector and
a heating element in thermal connection with the at least one object, wherein the at least one object is positioned such that emitted light passes the at least one object and/or is reflected by the at least one object and wherein the gas sensor is configured and arranged to activate the heating element as a reaction on detecting the contaminant, thereby vaporizing the contaminant on the at least one object in thermal connection with the heating element.

3. Gas sensor according to claim 1,
wherein the gas sensor further comprises
at least one object which is arranged in the path of the light between the light source and the detector and
a cleaning device configured and arranged to remove at least partially the contaminant from the at least one object, wherein the at least one object is positioned such that emitted light passes the at least one object and/or is reflected by the at least one object and
wherein the gas sensor is configured and arranged to trigger the cleaning device as a reaction on detecting the contaminant.

4. Gas sensor according to claim 1, wherein the gas sensor is configured to switch the adaptable filter system
between the first, second, and third composite states or
between the first, second, and fourth composite states.

5. Gas sensor according to claim 4, wherein the gas sensor is configured to detect that light received during the second composite state has been attenuated differently than light received during the third composite state.

6. Gas sensor according to claim 1,
wherein the gas sensor is configured to be selectively operated in a detecting mode in which the adaptable filter system is switched between the first and the fourth composite states or in a distinguishing mode in which the adaptable filter system is switched between at least three of the composite states and
wherein the gas sensor is further configured to switch from the detecting mode into the distinguishing mode if a positive alarm is detected in the detecting mode.

7. Gas sensor according to claim 1, wherein the first and second filters are arranged on the adaptable filter system in respective regions having respective first and second envelopes, wherein the first and second envelopes overlap.

8. Gas sensor according to claim 1, wherein the gas sensor is configured
to switch the first filter using a first input signal and
to switch the second filter using a second input signal, wherein the first input signal is a first square wave having a first frequency and wherein the second input signal is a second square wave having a second frequency.

9. Gas sensor according to claim 8, wherein the gas sensor is configured to switch the first and second filters, using synchronized input signals of the same frequency and to subsequently switch the first and second filters using the first and second input signals.

10. Gas sensor according to claim 1, wherein the detector is moveable with respect to the adaptable filter system.

11. Adaptable filter system for a gas sensor, wherein the adaptable filter system comprises
a first optical filter and
a second optical filter,
wherein the first filter is operable to switch between a first reference state in which the first filter passes light according to a first reference wavelength profile and a first measurement state in which the first filter passes light according to a first measurement wavelength profile,
wherein the second filter is operable, independently of the first filter, to switch between a second reference state in which the second filter passes light according to a second reference wavelength profile and a second measurement state in which the second filter passes light according to a second measurement wavelength profile, wherein the first reference wavelength profile is different from the second reference wavelength profile, the first and second filters, thereby being switchable between four different composite states, the four composite states comprising:
- a first composite state in which the first and second filters, are in the first and second reference states respectively,
- a second composite state in which the first filter is in the first reference state and the second filter is in the second measurement state,
- a third composite state in which the first filter is in the first measurement state and the second filter is in the second reference state, and
- a fourth composite state in which the first and second filters, are in the first and second measurement states respectively.

12. An adaptable filter system according to claim 11, in combination with a gas sensor comprising a light source and a detector, wherein the gas sensor is configured and arranged to detect at least one target gas and to detect at least one contaminant.

13. A method of operating a gas sensor configured and arranged to detect at least one target gas, wherein the gas sensor comprises a light source configured and arranged to emit light, a measurement volume, a detector configured and arranged to receive light, and an adaptable filter system, wherein the adaptable filter system comprises a first filter and a second filter, the method comprising the steps of:
- providing the first filter to be operable to switch between a first reference state in which the first filter passes light according to a first reference wavelength profile and a first measurement state in which the first filter passes light according to a first measurement wavelength profile;
- providing the second filter is to be operable, independently of the first filter, to switch between a second reference state in which the second filter passes light according to a second reference wavelength profile and a second measurement state in which the second filter passes light according to a second measurement wavelength profile, wherein the first reference wavelength profile is different from the second reference wavelength profile;

providing the first and second filters to be switchable between four different composite states, the four composite states comprising:
- a first composite state in which the first and second filters are in the first and second reference states respectively,
- a second composite state in which the first filter is in the first reference state and the second filter is in the second measurement state,
- a third composite state in which the first filter is in the first measurement state and the second filter is in the second reference state, and
- a fourth composite state in which the first and second filters are in the first and second measurement states respectively;

with the light source emitting light, wherein at least a part of the emitted light passes along a light path from the light source through the measurement volume and the adaptable filter system to the detector;

switching the adaptable filter system between at least three of the composite states;

with the detector generating a respective signal corresponding to light received by the detector for every one of the at least three used composite states; and determining a presence of a contaminant other than the target gas in the light path between the light source and the detector automatically, by comparing the respective detector signals generated during at least three of the composite states with each other.

14. Method according to claim 13,
wherein at least one object is arranged in the path of the light between the light source and the detector,
wherein at least a part of the light passes the at least one object and/or is reflected by the at least one object and
wherein as a reaction on detecting the contaminant the object is heated such that the contaminant is vaporized.

15. Method according to claim 13,
wherein the gas sensor is operated in a detecting mode and a subsequent distinguishing mode,
wherein the filter system in the detecting mode is switched between only two different composite states and in the distinguishing mode is switched between at least three different composite states.

* * * * *